US00PP23865P3

(12) United States Plant Patent
Pinochet

(10) Patent No.: US PP23,865 P3
(45) Date of Patent: Sep. 3, 2013

(54) **VARIETY OF *PRUNUS* ROOTSTOCK NAMED 'DENSIPAC'**

(50) Latin Name: ***Prunus besseyi*×*P. cerasifera***
Varietal Denomination: Densipac

(75) Inventor: Jorge Pinochet, Barcelona (ES)

(73) Assignee: Agromillora Iberia, S.L., Barcelona (ES)

( * ) Notice: Subject to any disclaimer, the term of this patent is extended or adjusted under 35 U.S.C. 154(b) by 193 days.

(21) Appl. No.: 13/065,946

(22) Filed: Apr. 1, 2011

(65) Prior Publication Data

US 2012/0255074 P1 Oct. 4, 2012

(51) Int. Cl.
*A01H 5/00* (2006.01)

(52) U.S. Cl.
USPC ..... Plt./184; Plt./180

(58) Field of Classification Search
USPC ..... Plt./184, 180
See application file for complete search history.

*Primary Examiner* — June Hwu
*Assistant Examiner* — Louanne Krawczewicz Myers
(74) *Attorney, Agent, or Firm* — The Webb Law Firm

(57) ABSTRACT

A new and distinct plum hybrid plant used as a rootstock that exhibits low vigor, good productivity, and is highly compatible with peach and nectarine varieties.

4 Drawing Sheets

Botanical classification: *Prunus besseyi*×*P. cerasifera*.
Varietal denomination: 'Densipac'.

BACKGROUND OF THE INVENTION

The present invention comprises a new and distinct cultivar of plum hybrid *Prunus besseyi*×*P. cerasifera* used as a rootstock known by the varietal name 'Densipac'. The new variety was discovered in Barcelona, Spain in 1998 as a result of a planned breeding program. The new variety is the result of a cross between an unnamed clone of *P. besseyi* (female parent, unpatented) and an unnamed clone of *P. cerasifera* (male parent, unpatented). The purpose of the breeding program was to develop a low vigor rootstock with good capacity to control vigor, adapted to Mediterranean conditions, compatible with peach and nectarine varieties, with a high tolerance to poorly drained clayish soils that suffer from waterlogging conditions. The new variety exhibits similar good tolerance to calcareous soils, moderate root-knot nematode resistance, and resistance to several soil-borne fungi, especially *Rosellinia necatrix*. The genotype has medium chilling requirements and good productivity. It differs from both parents in its leaf shape, vigor, and the fact that it better tolerates water logging conditions. Further, the new variety has similar vigor, tolerance to iron chlorosis, and root-knot nematode resistance to plum hybrid 'Saint Julien 655-2' (unpatented), but differs from 'Saint Julien 655-2' in its improved compatibility with peach, nectarine, and some almond varieties, no root suckering, lesion nematode resistance, resistance to *Rosellinia necatrix* (soil-borne fungus), leaf morphology, and lower chill requirements. The new variety has been trial and field tested and has been found to retain its distinctive characteristics and remain true to type through successive propagations. The following characteristics distinguish 'Densipac' from other varieties known to the breeder:

1. Low vigor with a small trunk cross-section area;
2. High capacity to control tree vigor when grafted with peach and nectarine varieties (recommended use);
3. High tolerance to root asphyxia;

4. Better tolerance to alkaline soils than most peach rootstocks;
5. Moderate resistance to root-knot nematodes (*Meloidogyne* spp.);
6. Resistance to the lesion nematode *Pratylenchus vulnus;*
7. Induces early fruit maturation in peach varieties;
8. Induces larger sized fruit in peach and nectarine varieties;
9. Medium chilling requirements within the range of 600 to 800 cu.; and
10. Resistance to the white root rot fungus *Rossellia necatrix.*

DESCRIPTION OF THE DRAWINGS

The accompanying photographic drawings illustrate the new variety with the color being as nearly true as is possible with color illustrations of this type.

DESCRIPTION OF THE PLANT

Figure 1:
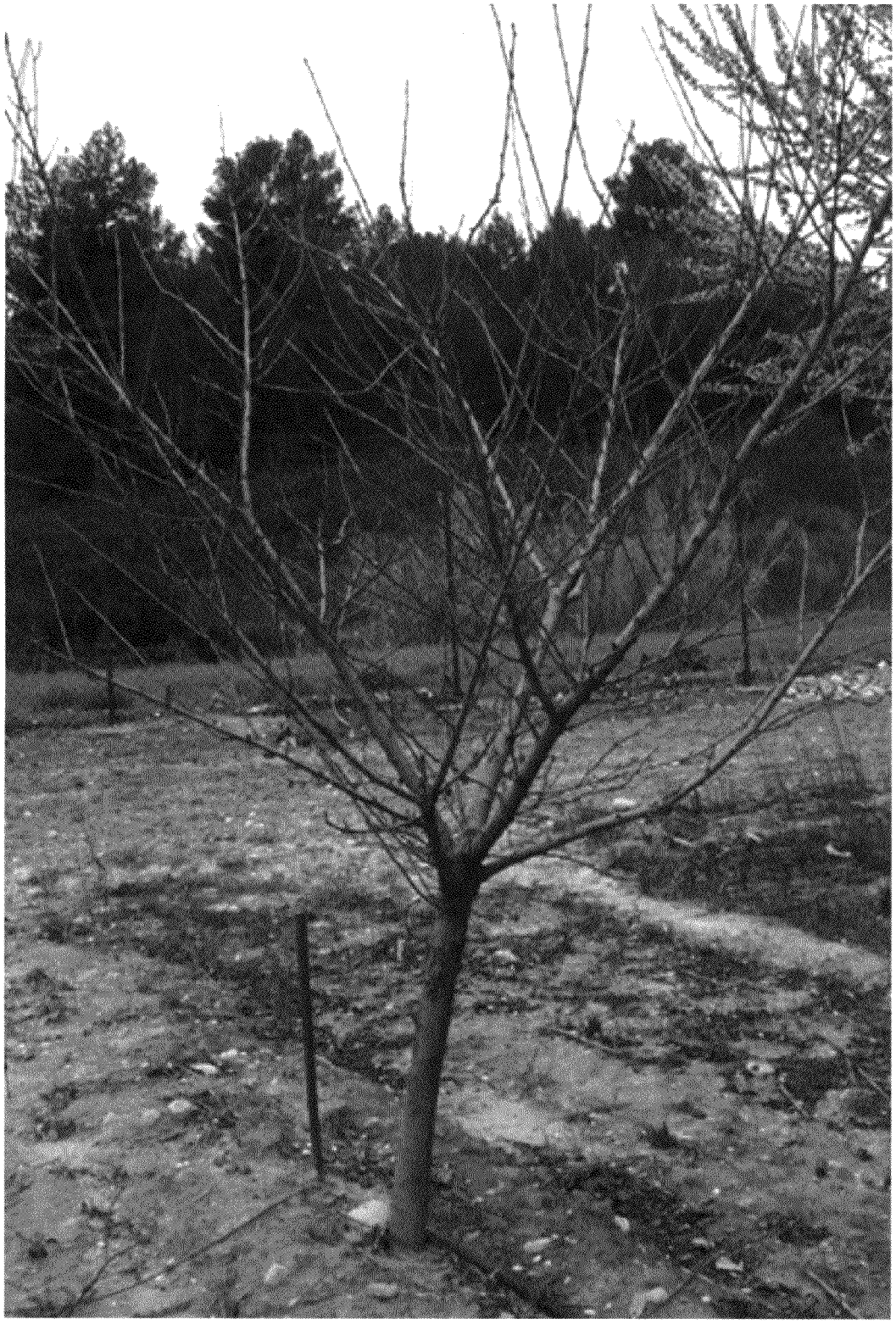
FIG. 1 shows an entire tree of the new variety.
Figure 2:
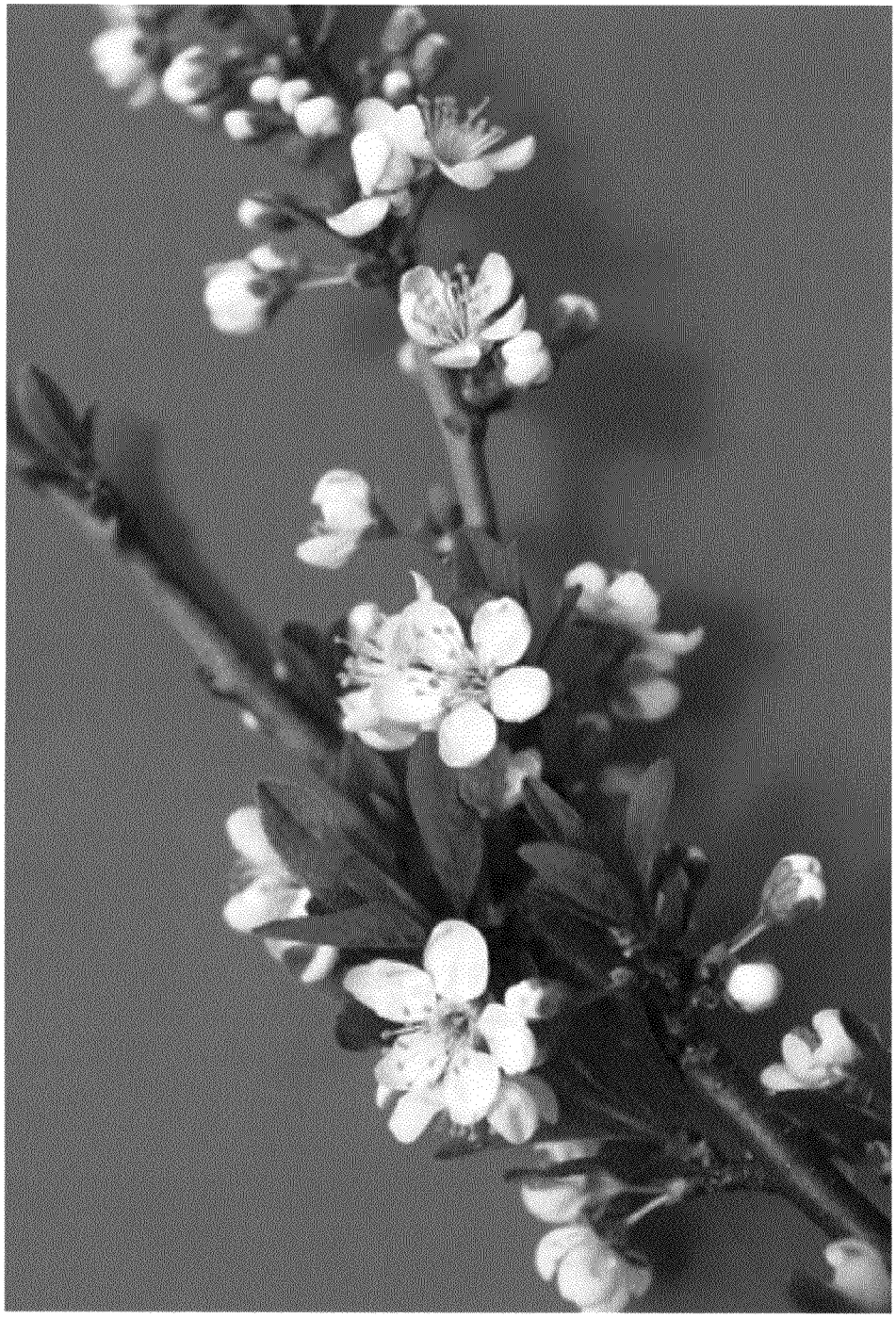
FIG. 2 shows the flowers of the new variety.
Figure 3:
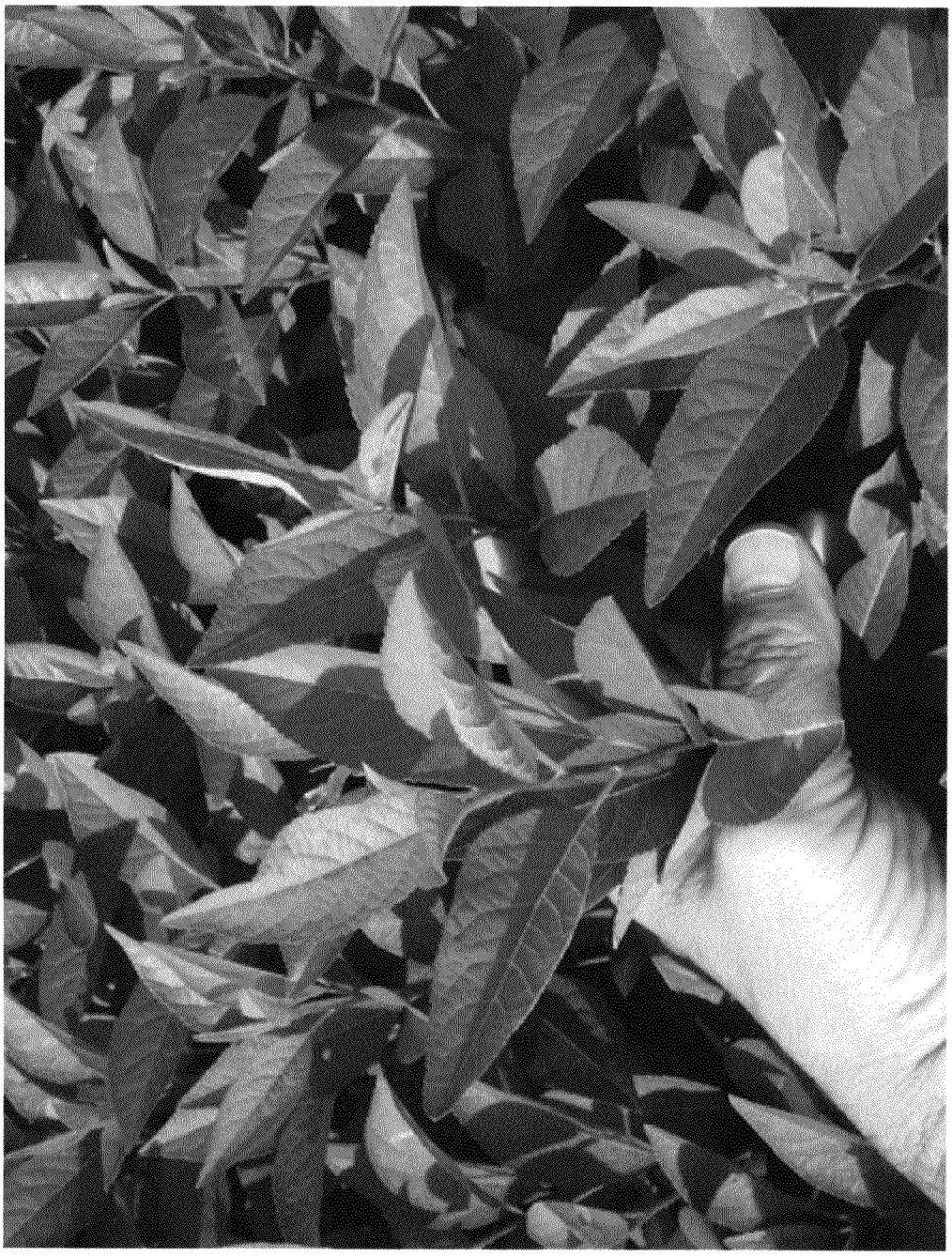
FIG. 3 shows the leaves of the new variety.
Figure 4:
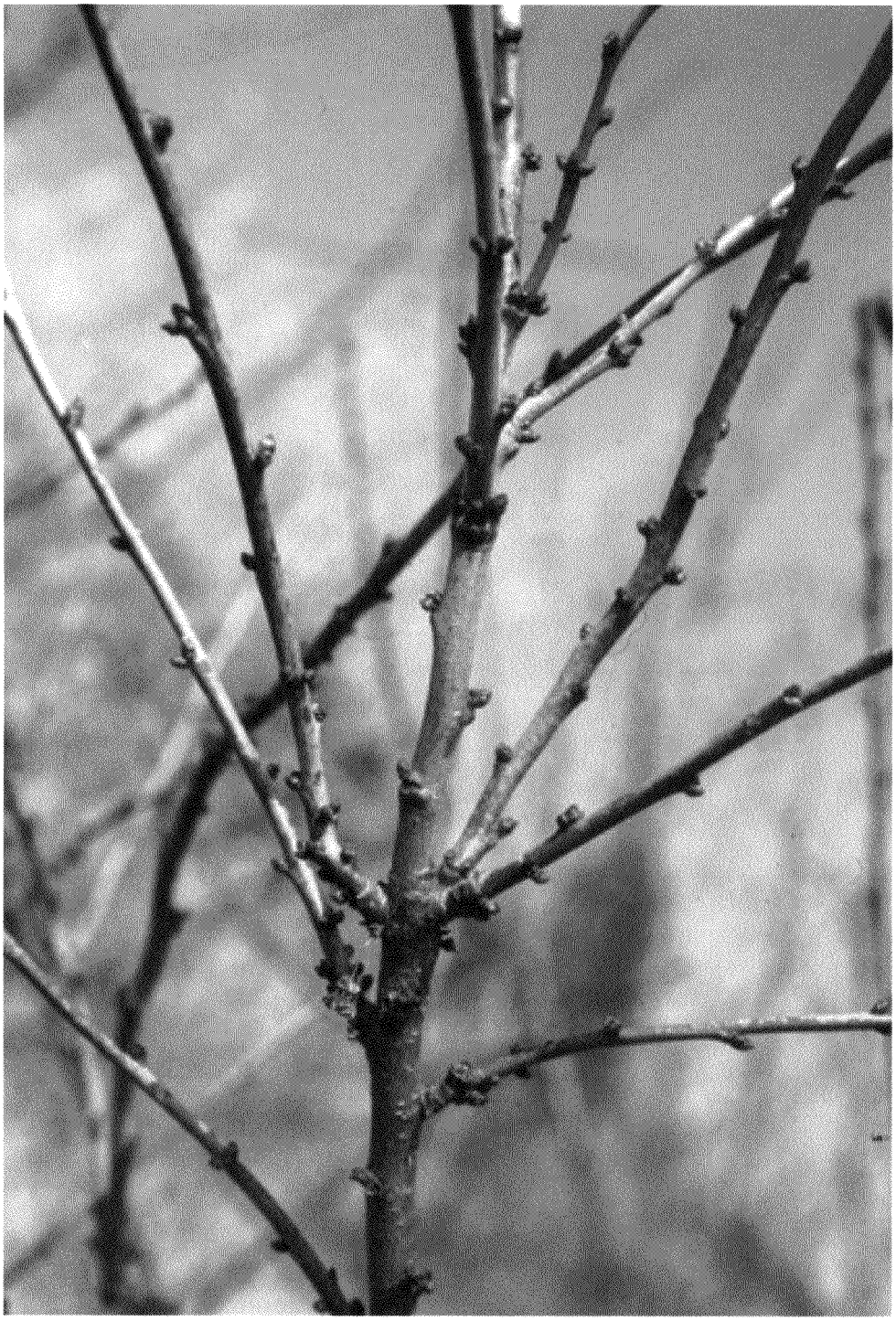
FIG. 4 shows the flower buds and branches of the new variety.

The following detailed description sets forth the characteristics of the new cultivar. The data which defines these characteristics was collected under natural daylight on plants produced by asexual reproductions via in vitro propagation carried out in Barcelona, Spain. The plants were grown under normal field conditions with drip irrigation and in 40 liter containers. Color designations are presented with reference to the "Dictionary of Color" by A. Maerz and M. Rea Paul, Second Edition (1950).

TREE

Age: 7 years.
Height: 2.2 meters.

Spread: Semi-erect.
Width: 1.4 meters.
Vigor: Low.
Density: Medium.
Form: Compact.
Production: Medium to abundant.
Growth type: Upright.
Bearing: Non-fruit bearing.
Pathogen resistance:
*Fungal disease.*—*Rosellinia necatrix* (soil borne fungus that causes white root rot in fruit trees).
*Insects.*—Unknown.
*Mites.*—Unknown.
*Viruses.*—Unknown.
*Other diseases.*—Root-knot nematodes (*Meloidogyne* spp.) and lesion nematodes (*Pratylenchus vulnus*).
Rootstock performance:
*Quality.*—Controls tree vigor; ideal for high density orchards.
*Root sprouts* (*suckering*).—Rare suckering present and only at crown level.
*Anchorage.*—Good with a big, fibrous root system.
*Compatibility.*—Compatible with peach, nectarine, almond, and plum varieties.
*Vigor.*—Low (40-45% less than 'Nemaguard' (*Prunus persica*×*P. davidiana*) (unpatented)).
Trunk:
*Size.*—Reduced trunk cross sectional area; from 12 to 14 cm. in diameter.
*Surface texture.*—Fairly smooth with longitudinal scarf-skin and horizontally oriented lenticels.
*Bark color.*—Plate 16, A 5 (Bear Chaetura Drab).
*Lenticels.*—Length: 10 to 19 mm. Width: 2 to 3 mm. Color: Plate 7, C 7 (Bonito Fuscous). Density: Low.
Branches:
*Diameter.*—Variable; from 0.5 to 1 cm. in the same growing season.
*Surface texture.*—Smooth in the current season with incipient longitudinal striae as maturity advances.
*Color.*—Plate 16, L 7 (Bronze Green).
*Form.*—Circular in diameter.
*Average angle.*—Acute.
*Bud arrangement.*—Helicoidal throughout the branch.
*Lenticels.*—Length: 1 to 2 mm. in the first year of growth. Width: 0.5 to 1 mm.
Shape: Rounded initially in younger tissue; elongated horizontally as branches mature into the season.
*Density.*—Low, but progressing to medium as maturity advances.
*Color.*—Plate 15, E 7 (Acorn Meadlowlark).
Leaves:
*Length.*—7 to 9 cm. (end of season).
*Width.*—3 to 4 cm.
*Form.*—Elliptic.
*Lower surface texture.*—Smooth.
*Upper surface texture.*—Pubescent.
*Thickness.*—Medium.
*Base.*—Acute.
*Apex.*—Acute.
*Margin.*—Crenate.
*Pubescence.*—Upper surface: Essentially absent; very tiny pubescence observed only with the aid of a dissecting scope. Lower surface: Absent.
*Color.*—Young leaves: Upper surface: Plate 23, E 11 (Monticello Green). Lower surface: Plate 29, B 4 (Celandine Green). Mature leaves: Upper surface: Plate 24, L 8. Lower surface: Plate 22, C 7 (Cactus).
*Petiole.*—Shape: Straight with a central groove along the upper side with 1 to 3 very small sized nectaries near the base of the leaf. Length: 11 to 15 mm. Diameter: 1.5 to 2 mm. Color: Plate 19, J 6 (Apple Green). Texture: Smooth with no pubescence present.
*Veins.*—Venation type: Tree type disposition. Color: Upper surface: Plate 20, K 6 (Piquant Green). Lower surface: Plate 19 F 4.
Flower buds:
*Pedicel.*—Length: 9 to 12 mm. Diameter: 1.5 to 2 mm. Color: Plate 18 B 7 (Aqua Green).
*Bud.*—Length: 1.5 to 1.8 mm. Width: 0.7 to 1.3 mm. Shape: Rounded to ovoid with a pointed apex. Color: Plate 14, I 10 (Cinnamon Brown).
Flowers:
*Bloom timing.*—Fourth week of March in Barcelona, Spain.
*Blooming period.*—10 to 15 days.
*Pollination requirements.*—None.
*Number of flowers per raceme.*—Normally 2.
*Fragrance.*—None present.
*Average width.*—14-16 mm.
*Average depth.*—7-10 mm.
*Petals.*—Number: 5. Length: 6 to 8 mm. Width: 4 to 6 mm. Shape: Rounded. Aspect: Cupped upwards and inwards. Margin: Slightly undulate. Texture and appearance: Smooth.
*Color.*—When opening (upper and lower surfaces): Plate 50, A 1. Fully opened (upper and lower surfaces): Plate 49, B 1.
*Sepals.*—Shape: Elliptic and rounded. Margin: Smooth. Texture: Pubescent. Length: 4 to 6 mm. Width: 2 to 3 mm. Color: Upper surface: Plate 21, B 7 (Tarragon). Lower surface: Plate 21, F 5 (Fern Green).
*Stamens.*—Number (per flower): 20 to 24. Filament length: 6 to 8 mm.
*Anthers.*—Shape: Kidney-shaped. Length: 1 to 1.3 mm. Color: Plate 11, I 2 (Malmaison).
*Pollen.*—Color: Plate 12, J 6 (Honey Middlestone). Amount: Abundant.
*Pistils.*—Length: 9 to 11 mm.
*Style.*—Length: 10 to 13 mm. Color: Plate 17, A 6 (Opaline Green).
*Stigma.*—Shape: Rounded. Color: Plate 13, D 2 (Bronze Clair).
Fruit description: None produced—trees are sterile.
Use: As a low vigor rootstock for mainly peach and nectarine varieties, but can also be used for plums.
Winter hardiness: Hardy (under the conditions in Spain).
Bud winter hardiness: High.
Tolerance to root asphyxia: Highly tolerant.
Drought tolerance: Moderately tolerant.
Disease resistance: Moderate root-knot nematode resistance, resistance to lesion nematodes, resistance to *Rosellinia necatrix* (white root rot), and resistant to Oidium.

I claim:

1. A new and distinct variety of plum hybrid plant, as illustrated and described herein.

* * * * *